United States Patent [19]

Willis et al.

[11] 4,289,658
[45] Sep. 15, 1981

[54] 2-[-(2'2'3'-TRIMETHYL-3'-CYCLOPENTEN-1'-yl)-ETHYLIDEN]-AND ETHYL]-CYCLOPENTANOLS

[75] Inventors: Brian J. Willis, Bergenfield; John M. Yurecko, Jr., Bayonne, both of N.J.

[73] Assignee: Fritzsche Dodge & Olcott Inc., New York, N.Y.

[21] Appl. No.: 77,037

[22] Filed: Sep. 19, 1979

[51] Int. Cl.³ .................. C07C 35/21; A61K 7/46
[52] U.S. Cl. .................. 252/522 R; 568/816
[58] Field of Search .................. 252/522; 568/816

[56] References Cited

U.S. PATENT DOCUMENTS 4,173,585  11/1979  Yoshida et al. .................. 568/816
4,241,228  12/1980  Yoshida et al. .................. 568/816

OTHER PUBLICATIONS

Chem. Ab. vol. 92:93959g, 1980.

Primary Examiner—John F. Niebling
Attorney, Agent, or Firm—Cooper, Dunham, Clark, Griffin & Moran

[57] ABSTRACT

The present invention relates to novel compounds useful as fragrance materials which have the structure

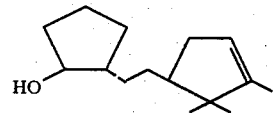

wherein the dashed line may be either a carbon-carbon single bond or a carbon-carbon double bond. The invention also provides methods of preparing these compounds from the reaction products of cyclopentanone, and 2,2,3-trimethyl-3-cyclopenten-1-acetaldehyde and fragrance compositions which include the compounds.

5 Claims, No Drawings

2-[-(2'2'3'-TRIMETHYL-3'-CYCLOPENTEN-1'-YL)-ETHYLIDEN]-AND ETHYL]-CYCLOPENTANOLS

BACKGROUND OF THE INVENTION

Chemicals having the cyclopentanol skeleton are known in the art of perfumery. Examples may be found in Actander, *Perfume and Flavor Chemicals* (1969). For example, iso-butenylcyclopentanol which has the structure

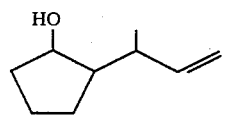

is identified as compound No. 376 in Actander. Its fragrance is described therein as powerful, herbaceous-floral odor of rather poor tenacity.

Actander compound No. 942 is dihydrocyclol which has the structure

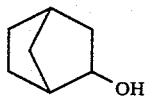

and is described as having a mild relatively sweet woody-piney odor of moderate tenacity.

Chemicals having the 2,3,3-trimethylcyclopentene skeleton are also known in the art of perfumery and flavor chemistry. For example, 2,2,3-trimethyl-3-cycopenten-1-acetaldehyde having the structure

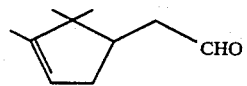

has been found in oils of *Juniperus communis L.* and *Lavandin*. The corresponding acid has been found in Olibanum oil.

U.S. Pat. No. 4,052,341 discloses the use in fragrance compositions of 3-methyl-5-(2,2,3-trimethylcyclopent-3-en-1-yl)pentan-2-ol which has the structure

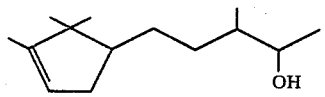

This compound is described as possessing a strong, precious woody odor reminiscent of Sandalwood oil.

SUMMARY OF THE INVENTION

In accordance with the present invention it has been found that compounds having the structure

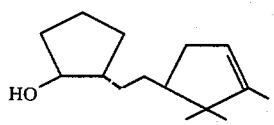

wherein the dashed line may be either a carbon-carbon single bond or carbon-carbon double bond are useful as fragrance materials. It will be recognized that the chemicals of this invention can exist in different stereoisomeric forms. The foregoing structural formula is intended to embrace the individual stereoisomers, as well as mixtures of the various stereoisomers of the substituted cyclic alcohols of this invention.

The present invention also provides efficient and economical processes for preparing these compounds. Thus, for example, the compound having the structure

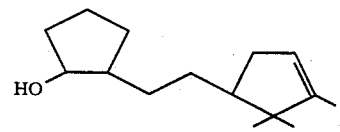

can be prepared by reacting cyclopentanone or a derivative of cyclopentanone, for example the morpholine enamine of cyclopentanone having the structure

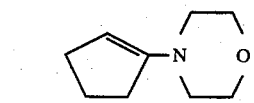

with 2,2,3-trimethyl-3-cyclopenten-1-acetaldehyde having the structure

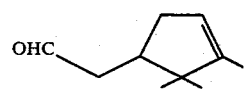

to produce compound having the structure

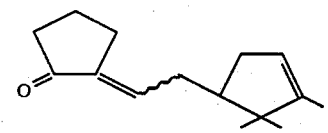

which upon hydrogenation yield compound 1.

Alternatively, compound 5 may be selectively reduced, for example, with sodium borohydride to yield a compound having the structure

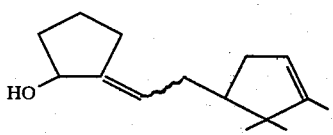

It has also been found that an admixture of compounds 1 and 2 is also useful as a fragrance material in place of either of the individual compounds.

Finally, in accordance with the present invention it has been found that fragrance compositions can be prepared by incorporating in these compositions Compound 1 or Compound 2 or a mixture thereof in amounts effective to impart fragrance to the composition.

DETAILED DESCRIPTION OF THE INVENTION

Compounds having the structure

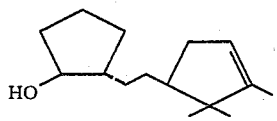

wherein the dashed line may be either a carbon-carbon single bond or a carbon-carbon double bond have been prepared. The compounds exhibit soft, warm woody notes with powdery nuances rendering these compounds useful as fragrance materials. These compounds exhibit similar odor characteristics and may be used individually or as mixtures in fragrance applications. Geometrical and optical isomers of these compounds may be separated by techniques known to the art. However, such separation is not necessary, since such mixtures of isomers can be employed directly without further separation.

Additionally, mixtures of these compounds wherein the dashed line may be either a carbon-carbon single bond or a carbon-carbon double bond exhibit fragrance properties similar to those of the individual compounds.

The following reaction scheme illustrates the various processes of the present invention for conveniently and inexpensively preparing such compounds:

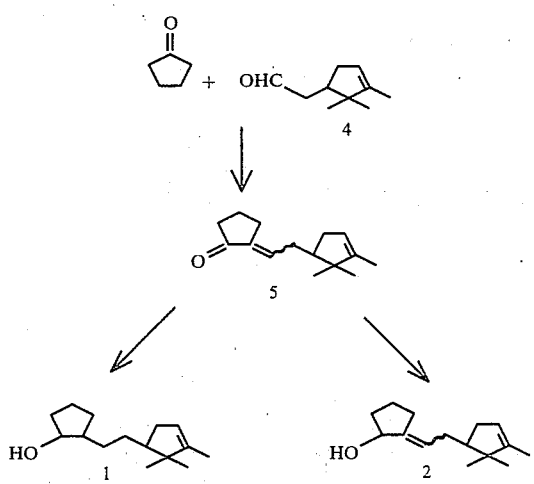

Specifically, Compound 1 can be prepared by Aldol condensation (see Modern Synthetic Reactions, chapter 10, by H.O. House) of cyclopentanone or a derivative of cyclopentanone, for example its morpholine enamine, with 2,2,3-trimethyl-3-cyclopenten-1-acetaldehyde 4 to provide directly, or after acidic work-up, the unsaturated ketone 5. Compound 5 is then hydrogenated by conventional techniques such as treatment with hydrogen at an elevated temperature and pressure in the presence of catalyst and a solvent to provide Compound 1.

Compound 2 may be prepared in an analagous manner. First, cyclopentanone is reacted with 2,2,3-trimethyl-3-cyclopenten-1-acetaldehyde to provide the Aldol condensation product 5. Compound 5 is then selectively reduced by treatment with a metal hydride such as di-isobutylaluminum hydride or with sodium borohydride to provide Compound 2. Mixtures of compounds 1 and 2 exhibit fragrance properties similar to those of either of the individual compounds. Therefore, such a mixture can be readily substituted for either compound in fragrance applications. Such a mixture can be prepared by mixing the seperately prepared compounds in desired amounts.

Compound 1, Compound 2 or a mixture thereof are readily incorporated into fragrance compositions for use in detergents, soaps, perfumes, bath preparations, hair preparations, cosmetics preparations, and the like. When so employed the compound or mixture should desirably be present in an amount from about 0.1% to about 80% by weight based upon the weight of the composition.

A number of examples are provided hereinafter to illustrate the preferred methods of synthesis of the compounds of this invention:

Gas Liquid Chromatography (GLC) analyses were obtained with a Hewlett-Packard Model 5840 A or Perkin-Elmer Model 3920 gas chromatograph using either a 10 ft, 2 mm ID glass column packed with 2% Carbowax 20 M on Chromosorb G 100/120, or a 12 ft, 2 mm Id glass column packed with 3% OV-101 on Chromosorb WHP 100/120. Nuclear Magnetic Resonance (NMR) spectra were recorded with a Varian Associates T-60A or XL 100 spectrometer, using tetramethylsilane as the internal reference. Infrared (IR) spectra were obtained with a Perkin-Elmer 137 infracord. Mass spectra (MS), were obtained with a Hewlett-Packard 5985 Mass Spectrometer.

Unless otherwise indicated weights are in grams, temperatures are in degrees centigrade and pressures are in mm Hg.

There are also set forth hereinafter several examples illustrating fragrance compositions which include the compounds of the present invention. All of these examples are intended only to illustrate the preferred embodiments of this invention and are not in any way intended to limit the scope thereof.

EXAMPLE 1

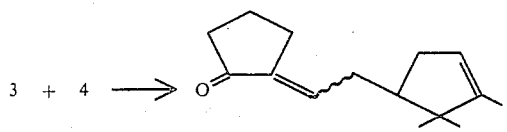

2,2,3-Trimethyl-3-cyclopenten-1-acetaldehyde (150 g), 1-morpholino-1-cyclopentene (154 g) and dry benzene (50 mL) were heated together at reflux for 24 h. The solution was cooled, aqueous 5% hydrochloric acid (400 mL) added, and the mixture stirred for 1.5 h at 20°. The organic layer was separated and washed successively with 5% hydrochloric acid (1 L), 5% sodium bicarbonate (300 mL) and water (4×150 mL). Solvent was removed, and the residue distilled to provide the desired product b$_{1.5}$ 128°–131°(143 g).

PMR(CDCL$_3$)δ0.8 (3H,), 1. (3H,), 1.6 (3H, bs) 5.2 (1H, bs), 6.4–6.8 (1H, m), 1.6–3.0 (9H, complex, IR (neat) 2995, 1750, 1540, 12,10, 810 cm$^{-1}$. MS (m/e, 109,93,

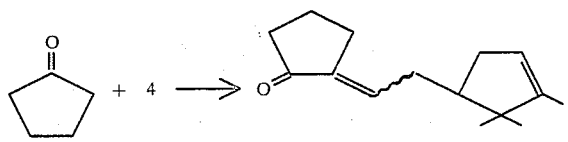

EXAMPLE 2

A solution of potassium hydroxide (86 g) in water (62 mL) and 2,2,3-trimethyl-3-cyclopenten-1-acetaldehyde (465 g) were added simultaneously, over 4 h to a vigorously stirred mixture of cyclopentanone (515 g) and water (610 mL) at about 0°. The mixture was stirred at 0° for a further 3 h, and then neutralized with hydrochoric acid. The reaction mixture was extracted with benzene (2×500 mL), and the combined organic extracts washed to neutrality. Solvent and unreacted cyclopentanone were removed by distillation. The residue was dissolved in benzene (1.5 L), oxalic acid (6 g) added, and the mixture heated at reflux for 20 h with removal of water formed using a Dean and Stark trap. The reaction mixture was cooled, washed to neutrality and, distilled to give an oil $b_{1.5}$ 125°–127° (310 g). Which was shown by GLC and spectral data to be the desired product.

EXAMPLE 3

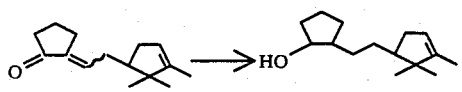

The product of Example 1 (120 g), butyl alcohol (70 mL), potassium hydroxide (50 mg) and cooper chromite (7 g) were charged to a 500 mL autoclave and the stirred mixture heated at 155°–160° under 300 psi of hydrogen. When gas uptake had ceased, the reactor was cooled (20°), evacuated, and purged with nitrogen. Solids were removed be filtration, solvent evaporated and the residue distilled to provide the desired product, $b_{0.5}$ 107°–110° (95 g). PMR (CDCL$_3$)$\delta$0.8 (3H,s), 1.0 (3H, s), 1.0 (3H,s), 4.1 (1H, bs), 5.2 (1H, bs), 1.2–3 (14H, complex), 1.2–2.0 1H, exchanged with D$_2$O). IR (neat) 3400, 2900, 1000, 910 cm$^{-1}$. MS(m/e) 107, 108, 93, 121, 222.

EXAMPLE 4

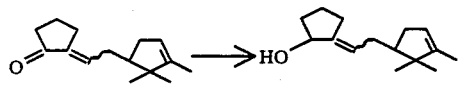

A solution of the product of Example 1 (99.6 g) in methanol (150 mL) was added dropwise, over 1.2 h to a stirred solution of sodium borohydride (13.0 g) in methanol (300 mL), with cooling, such that the reaction temperature was maintained at 0°–3°. When the addition was complete the reaction temperature was allowed to rise to 10° and agitation was continued for a further 4h. The mixture was acidified with dilute hyrochloric acid (25°) and the product extracted with ether. The organic layer was washed to neutrality, dried, and distilled to provide an oil $b_{1.5}$ 125°–127° (77.1 g) which was shown by GLC and spectral analysis to be a mixture of Compounds 2.

EXAMPLE 5

The following illustrates the utility of Compound 1 in fragrance compositions of the chypre type. Compound 1 is the novel compound of this invention as previously defined.

| pts/wt | CHYPRE Component |
|---|---|
| 260 | Oil Bergamot |
| 130 | Oil Orange Sweet |
| 200 | Methyl Ionone |
| 20 | Oil Rose |
| 50 | Jasmine Absolute |
| 5 | Oil Basil Sweet |
| 5 | Oil Estragon |
| 3 | Benzyl Salicylate |
| 3 | Oil Ylang Extra |
| 6 | Cinnamic Alcohol |
| 18 | Eugenol |
| 3 | Aldehyde C-14 |
| 2 | 10% Sol. Aldehyde C-12 MNA In Diethyl Phthalate Odorless |
| 10 | 10% Sol. Aldehyde C-11 Undecylenic in Phthalate Odorless |
| 10 | Civet Absolute |
| 40 | Coumarin |
| 35 | Labdanum Resinoid |
| 30 | Musk Ketone |
| 35 | Oakmoss Absolute |
| 35 | Oil Patchouly |
| 5 | Vanillin |
| 55 | Oil Vetiver Reunion |
| 100 | Compound 1 |
| 1000 | |

EXAMPLE 6

The following illustrates the utility of Compound 2 in fragrance compositions of the santal type. Compound 2 is the novel compound of this invention as previously defined.

| pts/wt | SANTAL Component |
|---|---|
| 90 | Terpineol |
| 220 | Oil Cedarwood |
| 50 | Oil Cassia |
| 80 | Coumarin |
| 40 | Musk Xylene |
| 80 | Oil Vetiver |
| 400 | Compound 2 |
| 40 | Resinoid Styrax |
| 1,000 | |

EXAMPLE 7

The following illustrates the utility of a mixture of compounds 1 and 2 as described in a fragrance composition exibiting a Sandalwood base fragrance.

| pts/wt | SANDALWOOD BASE Component |
|---|---|
| 20 | Oil Balsam Gurjon |
| 80 | Oil Amyris |
| 100 | Osyrol BBA |
| 800 | Mixture of Compounds 1 and 2 (50/50 w/w) |
| 1000 | |

As will be obvious to one skilled in the art many modifications, variations, and alterations can be made in the practices of this invention without departing from the spirit and scope thereof as set forth in the claims which follow.

What is claimed is:

1. The compound having the structure

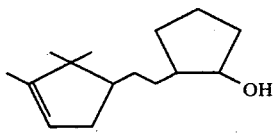

2. A fragrance composition which comprises an amount of the compound of claim 1 effective to impart fragrance thereto and conventional fragrance ingredients.

3. A fragrance composition in accordance with claim 2 wherein said effective fragrance-imparting amount is an amount from about 0.1% to about 80% by weight of said compound based upon the weight of said composition.

4. A method of preparing a fragrance composition which comprises incorporating in said composition an amount of the compound of claim 1 effective to impart fragrance thereto.

5. A method in accordance with claim 4 wherein said fragrance-imparting amount is an amount from about 0.1% to about 80% by weight of said compound based upon the weight of said composition.

* * * * *